United States Patent
Moncada et al.

(10) Patent No.: US 11,149,097 B2
(45) Date of Patent: Oct. 19, 2021

(54) ALIPHATIC SULFONYL AZIDE ANHYDRIDE FOR TIE LAYER

(71) Applicant: Dow Global Technologies LLC, Midland, MI (US)

(72) Inventors: Adriana I. Moncada, Midland, MI (US); Brian W. Walther, Clute, TX (US); Jerzy Klosin, Midland, MI (US); Ahmad E. Madkour, Canton, MI (US)

(73) Assignee: Dow Global Technologies LLC, Midland, MI (US)

( * ) Notice: Subject to any disclaimer, the term of this patent is extended or adjusted under 35 U.S.C. 154(b) by 475 days.

(21) Appl. No.: 16/310,912

(22) PCT Filed: Jun. 21, 2017

(86) PCT No.: PCT/US2017/038453
§ 371 (c)(1),
(2) Date: Dec. 18, 2018

(87) PCT Pub. No.: WO2017/223151
PCT Pub. Date: Dec. 28, 2017

(65) Prior Publication Data
US 2021/0221927 A1 Jul. 22, 2021

Related U.S. Application Data

(60) Provisional application No. 62/353,941, filed on Jun. 23, 2016.

(51) Int. Cl.
*C08F 8/34* (2006.01)
*C08F 10/02* (2006.01)
(Continued)

(52) U.S. Cl.
CPC ............ *C08F 8/34* (2013.01); *B32B 7/12* (2013.01); *B32B 27/08* (2013.01); *B32B 27/306* (2013.01);
(Continued)

(58) Field of Classification Search
None
See application file for complete search history.

(56) References Cited

U.S. PATENT DOCUMENTS 3,530,108 A    9/1970 Oppenlander
3,616,199 A   10/1971 Breslow
(Continued)

FOREIGN PATENT DOCUMENTS

CN    103059785 A    4/2013
WO    2016/109628 A1   7/2016

OTHER PUBLICATIONS

Bateman et al., Sulfonyl Azides—An Alternative Route to Polyolefin Modification, Journal of Applied Polymer Science, 2002, 84(7):1395-1402.

*Primary Examiner* — Ramsey Zacharia
(74) *Attorney, Agent, or Firm* — Quarles & Brady LLP

(57) ABSTRACT

The present disclosure provides a composition containing a sulfonamide aliphatic anhydride grafted olefin-based polymer. The present disclosure also provides a multilayer structure. In an embodiment, a multilayer film is provided and includes: a layer (A) comprising an olefin-based polymer; a layer (B) that is a tie layer comprising a sulfonamide aliphatic anhydride grafted olefin-based polymer (SAA-g-PO); and a layer (C) comprising a polar component.

15 Claims, 1 Drawing Sheet

Blown film sample
Machine direction →

2.54 cm x 15.24 cm strips cut

Thermally joined at 140°C at 0.3 seconds and 2.54 cm from one end

Tabs pulled to expose layer between tie layer and nylon. Exposed tabs placed into Instron tester to obtain adhesion force.

(51) Int. Cl.
    *B32B 27/08*     (2006.01)
    *B32B 27/30*     (2006.01)
    *B32B 27/32*     (2006.01)
    *B32B 27/34*     (2006.01)
    *B32B 7/12*     (2006.01)

(52) U.S. Cl.
    CPC .............. *B32B 27/32* (2013.01); *B32B 27/34* (2013.01); *C08F 10/02* (2013.01); *B32B 2250/03* (2013.01); *B32B 2250/04* (2013.01); *B32B 2250/05* (2013.01); *B32B 2250/24* (2013.01); *B32B 2307/732* (2013.01); *B32B 2307/748* (2013.01); *B32B 2439/70* (2013.01)

(56) References Cited

U.S. PATENT DOCUMENTS

| | | | |
|---|---|---|---|
| 3,701,788 A | 10/1972 | Sayigh et al. | |
| 4,031,068 A | 6/1977 | Cantor | |
| 4,515,636 A | 5/1985 | Carney et al. | |
| 4,666,631 A | 5/1987 | Udding | |
| 4,861,843 A | 8/1989 | Udding | |
| 4,935,466 A | 6/1990 | Udding | |
| 5,356,999 A * | 10/1994 | Kapuscinski | ........ C10M 167/00 |
| | | | 525/286 |
| 6,331,597 B1 | 12/2001 | Drumright et al. | |
| 6,521,306 B1 | 2/2003 | Hoenig et al. | |
| 6,552,129 B2 | 4/2003 | Babb et al. | |
| 7,399,808 B2 | 7/2008 | Walters et al. | |
| 2002/0156193 A1 | 10/2002 | Tau et al. | |
| 2011/0048512 A1 | 3/2011 | Chu et al. | |
| 2013/0123379 A1 | 5/2013 | Mcphee | |

* cited by examiner

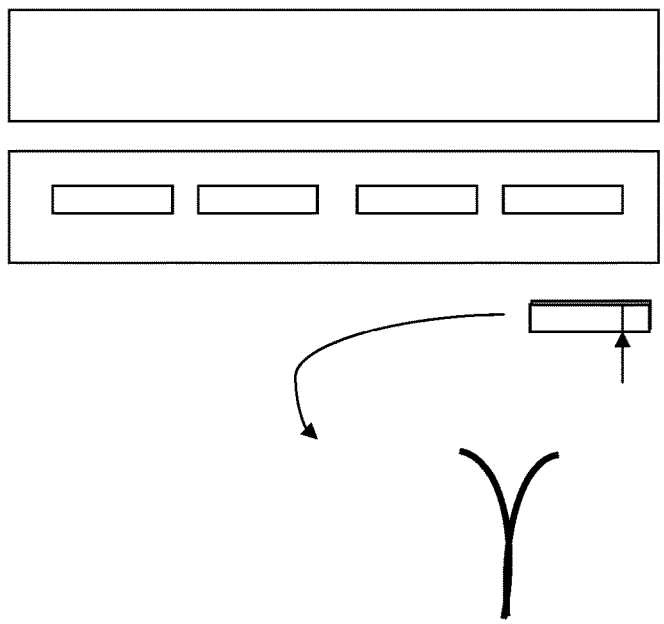

ALIPHATIC SULFONYL AZIDE ANHYDRIDE FOR TIE LAYER

BACKGROUND

The present disclosure relates to sulfonamide anhydride grafted olefin-based polymers, and sulfonamide aliphatic anhydride grafted olefin-based polymers in particular, and compositions and multilayer structures containing the same.

Tie layers containing maleic anhydride (MAH) grafted onto polyolefin (MAH-g-PO) are used in multilayer films for food packaging and specialty packaging. The MAH-g-PO tie layer is typically used to bind a polyolefin layer to other layers containing a polar substrate, such as nylon, for example. Currently, MAH-g-PO tie layer is produced via free radical grafting of MAH onto polyolefin in a melt blend process. However, free radical grafting is problematic because undesired crosslinking side chain reactions occur that affect the rheological properties (such as melt viscosity, for example) of the produced MAH-g-PO. In addition, when the polyolefin is polypropylene, undesired chain scission side reactions (resulting in lower molecular weight and higher melt flow rate) occur during free radical grafting. An alternative approach to produce MAH-g-PO that suppresses these challenges involves the grafting of aromatic sulfonyl azide anhydrides onto polyolefins via nitrene insertion (sulfonyl azide chemistry). However, the presence of aromatic groups in the tie layer is disadvantageous in certain applications because aromatic groups in polymers absorb UV light and may have a negative influence on aging and yellowing.

Desirable would be a polyolefin with non-aromatic functionalization that is not subject to crosslinking and/or chain scission during the production thereof.

SUMMARY

The present disclosure provides a composition containing a sulfonamide aliphatic anhydride-grafted-olefin-based polymer (SAA-g-PO) having a Structure (2):

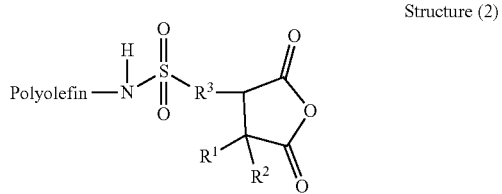

Structure (2)

wherein $R^1$, $R^2$, and $R^3$ may be the same or different; and $R^1$, $R^2$, and $R^3$ each is independently selected from a substituted $C_1$-$C_{40}$ hydrocarbonyl group, an unsubstituted $C_1$-$C_{40}$ hydrocarbonyl group, $Si(R^C)_3$, $OR^C$, $R^CC(O)O—$, $R^COC(O)—$, $R^CC(O)N(R)—$, $(R^C)_2NC(O)—$, a halogen atom, and a hydrogen atom, wherein $R^C$ is a $C_1$-$C_{30}$ hydrocarbonyl group;

with the proviso that at least one of $R^1$, $R^2$, and $R^3$ is selected from a substituted $C_1$-$C_{40}$ hydrocarbonyl group or an unsubstituted $C_1$-$C_{40}$ hydrocarbonyl group.

The nitrogen, N, in Structure (2) is bound to a carbon, C, of the polyolefin.

The present disclosure also provides a multilayer film. In an embodiment, a multilayer film is provided and includes:
a layer (A) comprising an olefin-based polymer;
a layer (B) that is a tie layer comprising a sulfonamide aliphatic anhydride grafted olefin-based polymer (SAA-g-PO); and
a layer (C) comprising a polar component.

The present disclosure provides another multilayer film. In an embodiment, a multilayer film is provided and includes:
a layer (A) comprising an olefin-based polymer;
a layer (B) that is a tie layer comprising a sulfonamide aliphatic anhydride grafted olefin-based polymer (SAA-g-PO);
a layer (C) comprising a polar component;
a layer (D) that is a tie layer, the layer (D) comprising the SAA-g-PO;
a layer (E) comprising an olefin-based polymer; and
the multilayer film has the structure A/B/C/D/E.

BRIEF DESCRIPTION OF THE DRAWING

FIG. 1 is a schematic representation of an adhesion force test in accordance with an embodiment of the present disclosure.

DEFINITIONS

Any reference to the Periodic Table of Elements is that as published by CRC Press, Inc., 1990-1991. Reference to a group of elements in this table is by the new notation for numbering groups.

For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

The numerical ranges disclosed herein include all values from, and including, the lower and upper value. For ranges containing explicit values (e.g., 1 or 2; or 3 to 5; or 6; or 7), any subrange between any two explicit values is included (e.g., 1 to 2; 2 to 6; 5 to 7; 3 to 7; 5 to 6; etc.).

Unless stated to the contrary, implicit from the context, or customary in the art, all parts and percents are based on weight and all test methods are current as of the filing date of this disclosure.

The term "composition" refers to a mixture of materials which comprise the composition, as well as reaction products and decomposition products formed from the materials of the composition.

The terms "blend" or "polymer blend," as used herein, is a blend of two or more polymers. Such a blend may or may not be miscible (not phase separated at molecular level). Such a blend may or may not be phase separated. Such a blend may or may not contain one or more domain configurations, as determined from transmission electron spectroscopy, light scattering, x-ray scattering, and other methods known in the art.

The terms "comprising," "including," "having" and their derivatives, are not intended to exclude the presence of any additional component, step or procedure, whether or not the same is specifically disclosed. In order to avoid any doubt, all compositions claimed through use of the term "comprising" may include any additional additive, adjuvant, or compound, whether polymeric or otherwise, unless stated to the contrary. In contrast, the term "consisting essentially of" excludes from the scope of any succeeding recitation any other component, step, or procedure, excepting those that are not essential to operability. The term "consisting of" excludes any component, step, or procedure not specifically delineated or listed. The term "or," unless stated otherwise, refers to the listed members individually as well as in any combination. Use of the singular includes use of the plural and vice versa.

A "hydrocarbon" is a compound that contains only hydrogen and carbon atoms. The hydrocarbon can be (i) branched or unbranched, (ii) saturated or unsaturated (iii) cyclic or acyclic, and (iv) any combination if (i)-(iii). Nonlimiting examples of hydrocarbons include alkanes, alkenes, and alkynes.

A "hydrocarbonyl group" is a hydrocarbon having a valence (typically univalent). Nonlimiting examples of hydrocarbonyl groups include alkyl-, cycloalkyl-, alkenyl-, alkadienyl-, cycloalkenyl-, cycloalkadienyl-, and alkynyl- groups.

A "substituted hydrocarbonyl" and a "substituted hydrocarbon" is a hydrocarbonyl group that contains a heteroatom.

An "unsubstituted hydrocarbonyl" and an "unsubstituted hydrocarbon" is a hydrocarbonyl group that contains only hydrogen and carbon atoms. An unsubstituted hydrocarbonyl excludes heteroatoms.

A "heteroatom" refers to an atom other than carbon or hydrogen. The heteroatom can be a non-carbon atom from Groups IV, V, VI and VII of the Periodic Table. Nonlimiting examples of heteroatoms include: F, N, O, P, B, S, and Si.

The term "alkyl" (or "alkyl group"), as described herein, refers to an organic radical derived from an aliphatic hydrocarbon by deleting one hydrogen atom therefrom. An alkyl group may be a linear, branched, cyclic or a combination thereof.

The term "aliphatic" refers to a hydrocarbon in which the carbon atoms form a cyclic chain or an open chain that is straight or branched. An aliphatic compound may be (i) branched or unbranched, (ii) cyclic or acyclic, (iii) saturated or unsaturated, or (iv) a combination of (i)-(iii). An aliphatic compound excludes aromatic compounds.

An "aromatic compound" is a hydrocarbon with one or more rings that contain alternating single and double bonds in its chemical structure. An aromatic compound excludes aliphatic compounds.

The term "polymer" is a macromolecular compound prepared by polymerizing monomers of the same or different type. "Polymer" includes homopolymers, copolymers, terpolymers, interpolymers, and so on. The term "interpolymer" refers to a polymer prepared by the polymerization of at least two types of monomers or comonomers. It includes, but is not limited to, copolymers (which usually refers to polymers prepared from two different types of monomers or comonomers), terpolymers (which usually refers to polymers prepared from three different types of monomers or comonomers), tetrapolymers (which usually refers to polymers prepared from four different types of monomers or comonomers), and the like.

The term "interpolymer," as used herein, refers to polymers prepared by the polymerization of at least two different types of monomers. The generic term interpolymer thus includes copolymers, usually employed to refer to polymers prepared from two different monomers, and polymers prepared from more than two different types of monomers.

The term "olefin-based polymer" (or "polyolefin" or "PO") is a polymer containing, in polymerized form, a majority weight percent of an olefin, for example ethylene or propylene, based on the total weight of the polymer. Nonlimiting examples of olefin-based polymers include ethylene-based polymers and propylene-based polymers. The terms "olefin-based polymer" and "polyolefin" are used interchangeably.

An "ethylene-based polymer" (or "polyethylene" or "PE") is a polymer that contains a majority weight percent polymerized ethylene monomer (based on the total weight of polymerizable monomers), and, optionally may contain at least one polymerized comonomer. The terms "ethylene-based polymer" and "polyethylene" are used interchangeably.

The terms "ethylene/alpha-olefin polymer" and "ethylene/α-olefin polymer," as used herein, refer to an interpolymer that comprises a majority weight percent polymerized ethylene monomer (based on the total weight of polymerizable monomers), and at least one polymerized α-olefin.

A "propylene-based polymer" is a polymer that contains a majority weight percent polymerized propylene monomer (based on the total weight of polymerizable monomers), and, optionally, may contain at least one comonomer.

DETAILED DESCRIPTION

A. Composition Containing a Sulfonamide Aliphatic Anhydride Grafted Olefin-Based Polymer The present disclosure provides a composition containing a sulfonamide aliphatic anhydride grafted olefin-based polymer (SAA-g-PO) having a Structure (2):

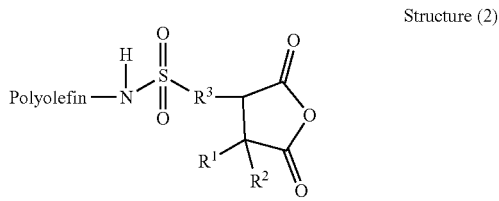

Structure (2)

wherein $R^1$, $R^2$, and $R^3$ may be the same or different; and $R^1$, $R^2$, and $R^3$ each is independently selected from a substituted $C_1$-$C_{40}$ hydrocarbonyl group, an unsubstituted $C_1$-$C_{40}$ hydrocarbonyl group, $Si(R^C)_3$, $OR^C$, $R^CC(O)O$—, $R^COC(O)$—, $R^CC(O)N(R)$—, $(R^C)_2NC(O)$—, a halogen atom, and a hydrogen atom, wherein $R^C$ is a $C_1$-$C_{30}$ hydrocarbonyl group;

with the proviso that at least one of $R^1$, $R^2$, and $R^3$ is selected from a substituted $C_1$-$C_{40}$ hydrocarbonyl group or an unsubstituted $C_1$-$C_{40}$ hydrocarbonyl group.

1. Base Olefin-Based Polymer

The base olefin-based polymer of the SAA-g-PO can be an ethylene-based polymer, a propylene-based polymer, and a combination thereof.

In an embodiment, the ethylene-based polymer is an ethylene/α-olefin polymer. Ethylene/α-olefin polymer may be a random ethylene/α-olefin polymer or an ethylene/α-olefin multi-block polymer. The α-olefin is selected from propylene, butene, methyl-1-pentene, hexene, octene, decene, dodecene, tetradecene, hexadecene, octadecene, cyclohexyl-1-propene (allyl cyclohexane), vinyl cyclohexane, and combinations thereof. The ethylene/α-olefin polymer has an α-olefin content of from 1 mole percent (mole %), or 4 mole %, or 5 mole %, or 10 mole % to 15 mole %, or 20 mole %, or 30 mole %. Mole % is based on the comonomers in the polymer.

In an embodiment, the ethylene/α-olefin copolymer is a homogeneously branched linear ethylene/α-olefin copolymer, or a homogeneous branched substantially linear interpolymer copolymer. Suitable α-olefins are discussed above. The terms "homogeneous" and "homogeneously-branched" are used in reference to an ethylene/α-olefin polymer, in which the α-olefin comonomer is randomly distributed within a given polymer molecule, and all of the polymer molecules have the same or substantially the same comonomer-to-ethylene ratio.

In an embodiment, the ethylene/α-olefin polymer is selected from ethylene/propylene copolymer, ethylene/butene copolymer, ethylene/1-hexene copolymer, ethylene/1-octene copolymer, linear low density polyethylene (LLDPE), low density polyethylene (LDPE), and combinations thereof.

In an embodiment, the ethylene/α-olefin copolymer has one, some, or all of the following properties: (i) a density from 0.87 g/cc, or 0.89 g/cc, or 0.90 g/cc, or 0.91 g/cc to 0.92 g/cc, or 0.93 g/cc, or 0.94 g/cc, or 0.95 g/cc or 0.96 g/cc; (ii) a melting point, Tm, from 80° C., 90° C., or 100° C., or 120° C. to 125° C., or 130° C., or 134° C., or 153° C., or 164° C.; and/or (iii) a melt flow (MF) (I2) from 0.3 g/10 min, or 0.5 g/10 min, or 1.0 g/10 min, or 2.0 g/10 min, or 6.0 g/10 min to 7 g/10 min, or 8 g/10 min, or 9 g/10 min, or 10 g/10 min, or 25 g/10 min, or 50 g/10 min.

In an embodiment, the ethylene/α-olefin copolymer is an ethylene/octene copolymer.

In an embodiment, the ethylene/α-olefin copolymer is an ethylene/1-hexene copolymer.

In an embodiment, the ethylene/α-olefin copolymer is a linear low density polyethylene (LLDPE). LLDPE is linear and does not contain long chain branching and is different than low density polyethylene (LDPE) which is branched or heterogeneously branched polyethylene. LDPE has a relatively large number of long chain branches extending from the main polymer backbone. LDPE can be prepared at high pressure using free radical initiators, and typically has a density from 0.915 g/cc to 0.940 g/cc. Nonlimiting examples of suitable LLDPE are polymers sold under the tradename DOWLEX, available from The Dow Chemical Company, Midland, Mich. In a further embodiment, the LLDPE is DOWLEX 2045 or DOWLEX 2045G.

In an embodiment, the ethylene-based polymer is an ethylene/α-olefin/diene terpolymer. An "ethylene/α-olefin/diene terpolymer" is a polymer with a majority weight percent (i.e., greater than 50 wt %) of units derived from ethylene, and also includes units derived from α-olefin comonomer, and units derived from a diene comonomer. The α-olefin comonomer is selected from $C_3$-$C_{12}$ α-olefin, or $C_3$-$C_8$ α-olefin. The diene can be conjugated-, non-conjugated-, straight chain-, branched chain- or cyclic-hydrocarbon diene having from 6 to 15 carbon atoms. Nonlimiting examples of suitable diene include 1,4-hexadiene; 1,6-octadiene; 1,7-octadiene; 1,9-decadiene; branched chain acyclic diene, such as 5-methyl-1,4-hexadiene; 3,7-dimethyl-1,6-octadiene; 3,7-dimethyl-1,7-octadiene; mixed isomers of dihydromyricene and dihydroocinene; single ring alicyclic dienes, such as 1,3-cyclopentadiene, 1,4-cyclohexadiene, 1,5-cyclooctadiene and 1,5-cyclododecadiene; and multi-ring alicyclic fused and bridged ring dienes, such as tetrahydroindene, methyl tetrahydroindene, dicyclopentadiene, and bicyclo-(2,2,1)-hepta-2,5-diene; alkenyl, alkylidene, cycloalkenyl and cycloalkylidene norbornenes, such as 5-methylene-2-norbornene (MNB), 5-propenyl-2-norbornene, 5-isopropylidene-2-norbornene, 5-(4-cyclopentenyl)-2-norbornene, 5-cyclohexylidene-2-norbornene, 5-vinyl-2-norbornene, norbornadiene, 5-ethylidene-2-norbornene (ENB), 5-vinylidene-2-norbornene (VNB), 5-methylene-2-norbornene (MNB), dicyclopentadiene (DCPD) and combinations thereof.

In an embodiment, the α-olefin is propylene comonomer and the ethylene/α-olefin/diene terpolymer is an ethylene/propylene/diene terpolymer. An "ethylene/propylene/diene polymer," or "EPDM," is as a polymer with a majority amount (greater than 50 wt %) of units derived from ethylene, and also includes units derived from propylene comonomer, and units derived from a diene comonomer.

The ethylene-based polymer may comprise two or more embodiments disclosed herein.

In an embodiment, the olefin-based polymer is a propylene-based polymer. Suitable propylene-based polymers include propylene homopolymers and propylene interpolymers. The polypropylene homopolymer can be isotactic, syndiotactic or atactic polypropylene. The propylene interpolymer can be a random or block copolymer, or a propylene-based terpolymer. Reactor copolymers of polypropylene may also be used. A nonlimiting example of a suitable propylene-based polymer is PRO-FAX™ 6361, available from LyondellBasell Industries Suitable comonomers for polymerizing with propylene include ethylene, butene, pentene, hexene, heptene, octene, nonene, decene, undecene, dodecene, as well as 4-methyl-1-pentene, 4-methyl-1-hexene, 5-methyl-1-hexene, vinylcyclohexane, and styrene. In an embodiment, the comonomers include ethylene, 1-butene, 1-hexene, and 1-octene.

2. Aliphatic Sulfonyl Azide Anhydride

The aliphatic sulfonyl azide anhydride used to prepare the SAA-g-PO, is an aliphatic sulfonyl azide anhydride with the Structure (1) below:

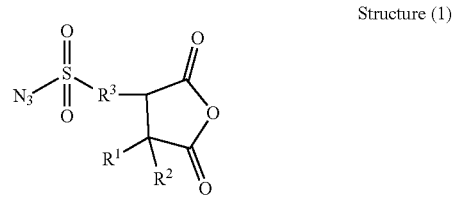

Structure (1)

wherein $R^1$, $R^2$, and $R^3$ may be the same or different; and $R^1$, $R^2$, and $R^3$ each is independently selected from a substituted $C_1$-$C_{40}$ hydrocarbonyl group, an unsubstituted $C_1$-$C_{40}$ hydrocarbonyl group, $Si(R^C)_3$, $OR^C$, $R^CC(O)O—$, $R^COC(O)—$, $R^CC(O)N(R)—$, $(R^C)_2NC(O)—$, a halogen atom, and a hydrogen atom, wherein $R^C$ is a $C_1$-$C_{30}$ hydrocarbonyl group;

with the proviso that at least one of $R^1$, $R^2$, and $R^3$ is selected from a substituted $C_1$-$C_{40}$ hydrocarbonyl group or an unsubstituted $C_1$-$C_{40}$ hydrocarbonyl group.

The $R^1$, $R^2$, and $R^3$ groups may or may not combine to form a ring structure comprising from 3, or 4 to 5, or 8, or 12, or 20, or 40, or 50 carbon atoms. In an embodiment, in the aliphatic sulfonyl azide anhydride of the Structure (1), at least two of the $R^1$, $R^2$, and $R^3$ groups combine to form a ring structure comprising from 3 to 50 carbon atoms. In another embodiment, in the aliphatic sulfonyl azide anhydride of the Structure (1), the $R^1$ and $R^3$ groups form an unsubstituted $C_3$-$C_8$, or $C_4$-$C_6$ hydrocarbonyl group ring structure.

In In an embodiment, in the aliphatic sulfonyl azide anhydride of the Structure (1), the $R^1$, $R^2$, and $R^3$ groups are not combined into a ring structure.

In an embodiment, the aliphatic sulfonyl azide anhydride of the Structure (1) includes one and only one azo functional group.

In an embodiment, in the aliphatic sulfonyl azide anhydride of the Structure (1), $R^2$ is hydrogen; and $R^1$ and $R^3$ form an unsubstituted $C_3$-$C_8$ hydrocarbonyl group ring structure. A nonlimiting example of a suitable aliphatic sulfonyl azide anhydride is 5-(azidosulfonyl)endo-cis-bicyclo[2.2.1]heptane-2,3-dicarboxylic anhydride, the structure of which is provided in Table 1A below as Structure (1a).

In an embodiment, in the aliphatic sulfonyl azide anhydride of the Structure (1), $R^1$ and $R^2$ each is hydrogen and $R^3$ is an unsubstituted or $C_1$-$C_8$ hydrocarbonyl group. A nonlimiting example of a suitable aliphatic sulfonyl azide anhydride is 3-(2,5-dioxotetrahydrofuran-3-yl)-2-methylpropane-1-sulfonyl azide, the structure of which is provided in Table 1A below as Structure (1b).

TABLE 1A

Structure (1a)

5-(azidosulfonyl)endo-cis-bicyclo[2.2.1]heptane-2,3-dicarboxylic anhydride

Structure (1b)

3-(2,5-dioxotetrahydrofuran-3-yl)-2-methylpropane-1-sulfonyl azide

In an embodiment, the aliphatic sulfonyl azide anhydride is selected from 5-(azidosulfonyl)endo-cis-bicyclo[2.2.1]heptane-2,3-dicarboxylic anhydride, 3-(2,5-dioxotetrahydrofuran-3-yl)-2-methylpropane-1-sulfonyl azide, and combinations thereof.

In an embodiment, the aliphatic sulfonyl azide anhydride has a limiting impact energy as determined by the BAM Fall Hammer Test from 10 Joules (J), or 15 J, or 20 J, or 25 J, or 30 J, or 35 J, or 40 J, or 45 J, or 50 J, or 55 J, or 60 J to 70 J, or 75 J, or 80 J, or 90 J, or 100 J, or 150 J, or 200 J. The "limiting impact energy" refers to the minimum amount of mechanical impact energy applied to a sample that causes ignition. The present aliphatic sulfonyl azide anhydride is stable because it is less contact-explosive than traditional azides, which have a limiting impact energy of less than 10 J. A limiting impact energy of greater than or equal to 10 J, and further greater than or equal to 20 J, indicates the present aliphatic sulfonyl azide anhydride is safe for a user to handle.

In an embodiment, the aliphatic sulfonyl azide anhydride has a half-life (neat), or a predicted half-life (neat), at 210° C. (DSC, isoconversional analysis) from 40 seconds (sec.), or 45 sec., or 50 sec., or 54 sec. to 60 sec., or 65 sec., or 70 sec., or 80 sec., or 90 sec., or 100 sec., or 150 sec. In another embodiment, the aliphatic sulfonyl azide anhydride has a half-life (in a blend with an ethylene/α-olefin copolymer at a concentration of 2.1 wt % aliphatic sulfonyl azide anhydride), or a predicted half-life (blend), at 210° C. (DSC, isoconversional analysis) from 50 sec., or 60 sec., or 70 sec., or 80 sec., or 85 sec. to 90 sec., or 100 sec., or 110 sec., or 120 sec., or 150 sec., or 200 sec., or 250 sec., or 300 sec. The "half-life" of a sulfonyl azide anhydride is the amount of time that passes before half of the molecules in the sulfonyl azide anhydride decompose, via conversion to the sulfonyl nitrene, at a certain temperature. The present aliphatic sulfonyl azide anhydride with a predicted half-life (neat) greater than 40 sec., and/or a predicted half-life (blend) greater than 50 sec. facilitates uniform dispersion of the azide moiety of the aliphatic sulfonyl azide anhydride during functionalization of a polyolefin.

The aliphatic sulfonyl azide anhydride may be produced in accordance with the procedures disclosed U.S. Application Ser. No. 62/353,919, filed on 23 Jun. 2016, incorporated herein by reference.

The aliphatic sulfonyl azide anhydride may comprise two or more embodiments disclosed herein.

3. Sulfonamide Aliphatic Anhydride Grafted Olefin-Based Polymer

The SAA-g-PO is formed by admixing the aliphatic sulfonyl azide anhydride with the olefin-based polymer and heating the admixture to at least the decomposition temperature of the aliphatic sulfonyl azide anhydride. The decomposition temperature is the temperature at which the aliphatic sulfonyl azide anhydride converts to the sulfonyl nitrene, eliminating nitrogen and heat in the process. In an embodiment, the olefin-based polymer and the aliphatic sulfonyl azide anhydride are dry blended to form a uniform mixture and this mixture is subsequently added to melt processing equipment, e.g., a melt extruder to achieve the grafting reaction, at a temperature that is at least the decomposition temperature of the aliphatic sulfonyl azide anhydride. The term "melt processing" (or "melt processing conditions") is a process in which the olefin-based polymer is softened or melted. Nonlimiting examples of suitable melt processing procedures include extrusion (including co-extrusion), pelletizing, film blowing, film casting, thermoforming, and compounding in polymer melt form.

Bounded by no particular theory, it is believed that under melt processing conditions, the aliphatic sulfonyl azide anhydride decomposes to form an intermediate singlet sulfonyl nitrene and nitrogen gas. The reactive singlet sulfonyl nitrene undergoes carbon-hydrogen bond insertion to form secondary sulfonamide linkages to the backbone of the olefin-based polymer, thereby producing a SAA-g-PO with the Structure (2):

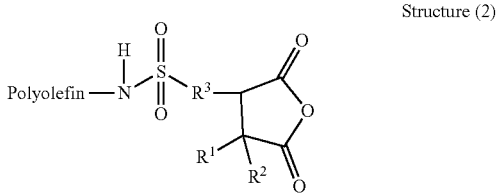

Structure (2)

The nitrogen, N, in Structure (2) is bound to a carbon, C, of the polyolefin.

In an embodiment, the aliphatic sulfonyl azide anhydride is the 5-(azidosulfonyl)endo-cis-bicyclo[2.2.1]heptane-2,3-dicarboxylic anhydride of the Structure (1a) provided above in Table 1A. Under melt processing conditions, the 5-(azidosulfonyl)endo-cis-bicyclo[2.2.1]heptane-2,3-dicarboxylic anhydride decomposes to form an intermediate singlet sulfonyl nitrene and nitrogen gas. The reactive singlet sulfonyl nitrene undergoes carbon-hydrogen bond insertion to form secondary sulfonamide linkages to the backbone of the olefin-based polymer, thereby producing a sulfonamide endo-cis-bicyclo[2.2.1]heptane-2,3-dicarboxylic anhydride grafted polyolefin or "bicyclo SAA-g-PO" with the Structure (2a) provided in Table 1B below. The nitrogen, N, in Structure (2a) is bound to a carbon, C, of the polyolefin.

In an embodiment, the aliphatic sulfonyl azide anhydride is the 3-(2,5-dioxotetrahydrofuran-3-yl)-2-methylpropane-1-sulfonyl azide of the Structure (1b) provided above in Table 1A, and the SAA-g-PO is a sulfonamide 3-(2,5-dioxotetrahydrofuran-3-yl)-2-methylpropane grafted polyolefin or "branched SAA-g-PO" with the Structure (2b) provided in Table 1B below. The nitrogen, N, in Structure (2b) is bound to a carbon, C, of the polyolefin.

TABLE 1B

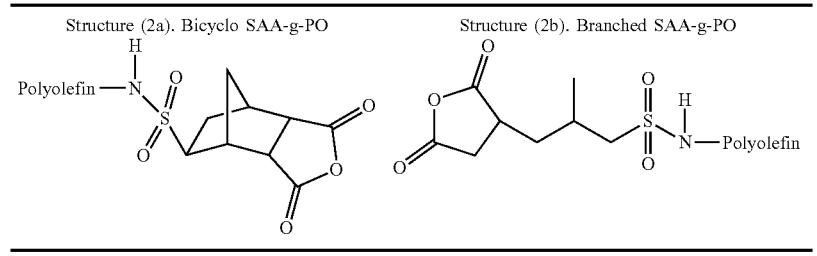

When the aliphatic sulfonyl azide anhydride is grafted to the olefin-based polymer, a sulfonamide aliphatic anhydride grafted olefin-based polymer (SAA-g-PO) is formed. Applicant discovered the aliphatic sulfonyl azide anhydride grafting reaction occurs with little, or no, crosslinking.

In an embodiment, the olefin-based polymer is an ethylene/α-olefin copolymer and the aliphatic sulfonyl azide anhydride is selected from 5-(azidosulfonyl)endo-cis-bicyclo[2.2.1]heptane-2,3-dicarboxylic anhydride, 3-(2,5-di oxotetrahydrofuran-3-yl)-2-methylpropane-1-sulfonyl azide, and combinations thereof. The ethylene/α-olefin copolymer and the aliphatic sulfonyl azide anhydride are admixed under melt processing conditions to produce a sulfonamide aliphatic anhydride grafted ethylene-based polymer (SAA-g-PE) with a grafting efficiency (GE) from at least 50%, or 60%, or 70%, or 80% to 90%, or 95%, or 99%. In a further embodiment, the SAA-g-PE contains maleic anhydride in an amount from 0.1 wt %, or 0.2 wt %, or 0.3 wt %, or 0.4 wt %, or 0.5 wt %, or 0.6 wt % to 0.7 wt %, or 0.8 wt %, or 0.9 wt %, or 1.0 wt %, or 1.1 wt %, or 1.5 wt %, or 2.0 wt %, or 10 wt %. Weight percent maleic anhydride is based on the total weight of the SAA-g-PE.

In an embodiment, the melt blend further comprises an antioxidant. A nonlimiting example of a suitable antioxidant is Irganox 1010, available from Ciba Specialty Chemicals. In an embodiment, the melt blend contains from greater than 0 wt %, or 0.01 wt % to 0.04 wt %, or 0.05 wt % antioxidant. In an embodiment, the melt blend contains 0.05 wt % antioxidant.

In an embodiment, the SAA-g-PO is a sulfonamide 3-(2,5-dioxotetrahydrofuran-3-yl)-2-methylpropane grafted ethylene-based polymer or "branched SAA-g-PE." In a further embodiment, the SAA-g-PO is a sulfonamide 3-(2,5-dioxotetrahydrofuran-3-yl)-2-methylpropane grafted LLDPE or "branched SAA-g-LLDPE."

In an embodiment, the SAA-g-PO is a sulfonamide endo-cis-bicyclo[2.2.1]heptane-2,3-dicarboxylic anhydride grafted ethylene-based polymer or "bicyclo SAA-g-PE." In a further embodiment, the SAA-g-PO is a sulfonamide endo-cis-bicyclo[2.2.1]heptane-2,3-dicarboxylic anhydride grafted LLDPE or "bicyclo SAA-g-LLDPE."

The SAA-g-PO may comprise two or more embodiments disclosed herein.

The composition may comprise two or more embodiments disclosed herein.

B. Multilayer Structure

The present disclosure provides a multilayer structure, and further a multilayer film, with a layer containing the composition with the SAA-g-PO. In an embodiment, the layer is a tie layer.

The present disclosure provides a multilayer structure. In an embodiment, the multilayer structure is a multilayer film and includes:

a layer (A) comprising an olefin-based polymer;

a layer (B) that is a tie layer comprising a sulfonamide aliphatic anhydride grafted olefin-based polymer (SAA-g-PO); and a layer (C) comprising a polar component.

1. Layer (A)

The layer (A) includes one or more olefin-based polymer(s). The olefin-based polymer of layer (A) can be any olefin-based polymer as disclosed for the base olefin-based polymer of the SAA-g-PO.

In an embodiment, the olefin-based polymer is an ethylene-based polymer. In an embodiment, the ethylene-based polymer is an ethylene/α-olefin polymer. In another embodiment, the ethylene-based polymer is an ethylene/α-olefin copolymer. In an embodiment, the ethylene/α-olefin copolymer is a LLDPE.

In an embodiment, the olefin-based polymer is a propylene-based polymer.

Layer (A) can be a blend of two or more olefin-based polymers as disclosed herein.

Layer (A) may comprise two or more embodiments disclosed herein.

2. Layer (B)

The present multilayer structure includes a layer (B) that is a tie layer. The tie layer is located between the layer (A) and the layer (C) thereby bonding, or otherwise attaching, the layer (A) to the layer (C).

In an embodiment, the layer (B) directly contacts the layer (A). The term "directly contacts," as used herein, is a layer configuration whereby a first layer is located immediately adjacent to a second layer and no intervening layers, or no intervening structures, are present between the first layer and the second layer.

The tie layer, layer (B), includes a sulfonamide aliphatic anhydride grafted olefin-based polymer (SAA-g-PO). The SAA-g-PO may be any SAA-g-PO disclosed herein. The base olefin-based polymer of the SAA-g-PO may be the same or different than the olefin-based polymer of layer (A). In an embodiment, the base olefin-based polymer of the SAA-g-PO is the same as the olefin-based polymer of layer (A). In another embodiment, the base olefin-based polymer of the SAA-g-PO is different than the olefin-based polymer of layer (A).

In an embodiment, the tie layer (B) includes an sulfonamide endo-cis-bicyclo[2.2.1]heptane-2,3-dicarboxylic anhydride grafted polyolefin or "bicyclo SAA-g-PO" of the Structure (2a) provided in Table 1B above.

In an embodiment, the tie layer (B) includes a sulfonamide 3-(2,5-dioxotetrahydrofuran-3-yl)-2-methylpropane grafted polyolefin or "branched SAA-g-PO" of the Structure (2b) provided in Table 1B above.

Not wishing to be bound by any particular theory, Applicants believe a tie layer containing the sulfonamide aliphatic anhydride grafted olefin-based polymer would exhibit less absorbance in the UV range compared to a tie layer containing a sulfonamide aromatic anhydride grafted olefin-based polymer because aliphatic compounds typically exhibit less absorbance in the UV range compared to aromatic compounds. A multilayer film with a tie layer containing the sulfonamide aliphatic anhydride grafted olefin-based polymer does not yellow after exposure to florescent lights, which is known to occur with multilayer films having a tie layer containing sulfonamide aromatic anhydride grafted olefin-based polymer.

Layer (B) can be a blend of two or more SAA-g-POs as disclosed herein.

Layer (B) may comprise two or more embodiments disclosed herein.

3. Layer (C)

The present multilayer structure includes a layer (C). The layer (C) includes a polar component. The layer (B) is a tie layer and is located between the layer (A) and the layer (C) thereby bonding, or otherwise attaching the layer (A) to the layer (C).

In an embodiment, the layer (B) tie layer directly contacts the layer (C). In a further embodiment, the layer (B) directly contacts the layer (A) (on a first side of layer (B)) and the layer (B) directly contacts the layer (C) (on a second side that is opposite the first side of the layer (B)), providing the multilayer film with the following layer configuration: A/B/C.

The layer (C) includes a polar component. Nonlimiting examples of suitable polar components include metal foil, polyamide (such as Nylon 6; Nylon 6/6; Nylon 6/66; Nylon 6/12; Nylon 12; etc.), ethylene/vinyl alcohol (EVOH) copolymer, polybutylene terephthalate (PBT), polyethylene terephthalate (PET), ethylene/acrylic acid (EAA) copolymer, ethylene/methacrylic acid (EMAA) copolymer, polylactic acid, cellulosic material (such as paper), and combinations thereof.

In an embodiment, the polar component is a polar polymer. A "polar polymer" is a polymer molecule with a permanent dipole, i.e., the polymer molecule has a positive end and a negative end. In other words, the electrons in a polar molecule are not shared equally among the atoms of the molecule. In contrast, a "nonpolar polymer" is a polymer molecule that does not have a permanent dipole, i.e., the polymer does not have a positive end and a negative end. The electrons in a nonpolar molecule are essentially equally shared among the atoms of the molecule. Most hydrocarbon liquids and polymers are nonpolar. Nonlimiting examples of suitable polar polymers include polymers containing a reactive proton such as in a hydroxyl (—OH) or amino (—NH) functionality.

Layer (C) can be a blend of two or more polar components as disclosed herein.

Layer (C) may comprise two or more embodiments disclosed herein.

Under melt processing conditions, the SAA-g-PO in layer (B) forms at least one linkage with the polar component in the layer (C). The linkage has the Structure (3).

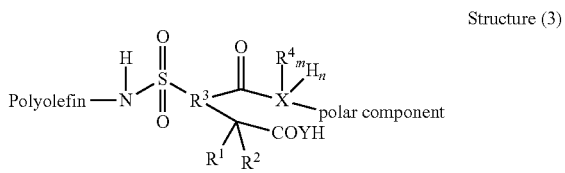

Structure (3)

wherein the nitrogen, N, is bound to a carbon, C, of the polyolefin;

wherein $R^1$, $R^2$, and $R^3$ may be the same or different; and $R^1$, $R^2$, and $R^3$ each is independently selected from a substituted $C_1$-$C_{40}$ hydrocarbonyl group, an unsubstituted $C_1$-$C_{40}$ hydrocarbonyl group, $Si(R^C)_3$, $OR^C$, $R^CC(O)O$—, $R^COC(O)$—, $R^CC(O)N(R)$—, $(R^C)_2NC(O)$—, a halogen atom, and a hydrogen atom, wherein R is a $C_1$-$C_{30}$ hydrocarbonyl group;

with the proviso that at least one of $R^1$, $R^2$, and $R^3$ is selected from a substituted $C_1$-$C_{40}$ hydrocarbonyl group or an unsubstituted $C_1$-$C_{40}$ hydrocarbonyl group;

X is selected from O, P, S, and N;

Y is selected from O, S, PH, PR, NH, and NR;

$R^4$ is a $C_1$-$C_8$ alkyl group;

m and n each independently is 0 or 1 with the proviso when m=1, n=0, and when n=1, m=0. In other words, Structure (3) contains $R_m$ or $H_n$.

In an embodiment, X of Structure (3) is derived from the polar component.

In an embodiment, Y of Structure (3) is oxygen, or O. In another embodiment, Y of Structure (3) is oxygen, O; X of Structure (3) is nitrogen, N; m=0; and n=1.

In an embodiment, the multilayer film includes:
layer (A) composed of an ethylene/α-olefin copolymer;
layer (B) composed of SAA-g-PE; and
layer (C) composed of a polyamide (such as nylon).
Layer (B) is in direct contact with layer (A) and layer (C).
The multilayer film has a peel strength from 400 N/m, or 500 N/m, or 548 N/m, or 700 N/m to 1,138 N/m, or 1,200 N/m as measured in accordance with the T-Peel test.

The present multilayer structure, and further the present multilayer film, can have three layers, or more than three layers. For example, the multilayer structure, and further the multilayer film, can have four, five, six, seven, eight, nine, ten, eleven, or more layers.

In an embodiment, the multilayer film includes:
layer (A) comprising an olefin-based polymer;
layer (B) that is a tie layer comprising the SAA-g-PO;
layer (C) comprising a polar component;
a layer (D) that is a tie layer, the layer (D) comprising the SAA-g-PO; and
a layer (E) comprising an olefin-based polymer,
wherein the multilayer film has the structure A/B/C/D/E.

The SAA-g-PO in the layer (D) can be the same or different than the SAA-g-PO in layer (B). In an embodiment, the SAA-g-PO in layer (D) is the same as the SAA-g-PO in layer (B). In another embodiment, the SAA-g-PO in layer (D) is different than the SAA-g-PO in layer (B).

The olefin-based polymer in layer (E) can be the same or different than the olefin-based polymer in layer (A). In an embodiment, the olefin-based polymer in layer (E) is the same as the olefin-based polymer in layer (A). In another embodiment, the olefin-based polymer in layer (E) is different than the olefin-based polymer in layer (A).

In an embodiment, the five layer multilayer film has a thickness from 0.00762 millimeters (mm) (0.3 mils), or 0.0508 mm (2.0 mils) to 0.1016 mm (4.0 mils), or 0.508 mm (20 mils).

In an embodiment at least one of tie layer (B) and tie layer (D) directly contacts the layer (C).

In an embodiment, the layer (B) and the layer (D) each directly contact the layer (C). The SAA-g-PO in layer (B) and the SAA-g-PO in layer (D) each form at least one linkage with the polar component of the layer (C). The linkages have the Structure (3) provided above.

In an embodiment, the multilayer film includes:
layer (A) composed of an ethylene/α-olefin copolymer;
layer (B) composed of bicyclo SAA-g-PE and/or branched SAA-g-PE;
layer (C) composed of a polyamide (such as nylon);
a layer (D) composed of bicyclo SAA-g-PE and/or branched SAA-g-PE; and
a layer (E) composed of an ethylene/α-olefin copolymer.

In an embodiment, the layer (B) and the layer (D) each directly contact a nylon in layer (C). The bicyclo SAA-g-PE and/or the branched SAA-g-PE in layer (B) and the bicyclo SAA-g-PE and/or the branched SAA-g-PE in layer (D) forms imide linkages with the nylon in layer (C).

In an embodiment, layers (A) and (E) are each composed of an LLDPE that is an ethylene/1-octene copolymer, the layers (B) and (D) are each composed of bicyclo SAA-g-ethylene/1-octene copolymer, and the layer (B) and the layer (D) each directly contact the nylon in layer (C). In an embodiment, the multilayer film has a peel strength from 400 N/m, or 500 N/m, or 600 N/m, or 650 N/m, or 675 N/m to 700 N/m, or 1000 N/m, or 1100 N/m or 1200 N/m as measured in accordance with the T-Peel test.

In an embodiment, the multilayer film includes:
layer (A) composed of an ethylene/α-olefin copolymer;
layer (B) composed of bicyclo SAA-g-PE and/or branched SAA-g-PE;
layer (C) composed of EVOH copolymer;
a layer (D) composed of bicyclo SAA-g-PE and/or branched SAA-g-PE; and
a layer (E) composed of an ethylene/α-olefin copolymer.

In an embodiment, the layer (B) and the layer (D) each directly contact a nylon in layer (C). The bicyclo SAA-g-PE and/or the branched SAA-g-PE in layer (B) and the bicyclo SAA-g-PE and/or the branched SAA-g-PE in layer (D) forms linkages with the EVOH copolymer in layer (C).

In an embodiment, layers (A) and (E) are each composed of an LLDPE that is an ethylene/1-octene copolymer, the layers (B) and (D) are each composed of bicyclo SAA-g-ethylene/1-octene copolymer, and the layer (B) and the layer (D) each directly contact the EVOH copolymer in layer (C). In an embodiment, the multilayer film has a peel strength from 400 N/m, or 500 N/m, or 550 N/m, or 565 N/m, or 600 N/m to 700 N/m, or 1000 N/m, or 1100 N/m or 1200 N/m as measured in accordance with the T-Peel test.

In an embodiment, the five-layer film with A/B/C/D/E layer configuration is formed as a blown multilayer film with neighboring layers in direct contact with each other. The blown multilayer film has a thickness from 0.3 mils, or 2.0 mils to 4.0 mils, or 20 mils and has an adhesion force from 400 N/m, or 500 N/m, or 550 N/m, or 600 N/m, or 700 N/m to 800 N/m, or 900 N/m, or 1000 N/m, or 1200 N/m.

The multilayer structure may comprise two or more embodiments disclosed herein.

The present disclosure also provides an article containing the multilayer structure, such as a food package or a specialty package.

Test Methods

Density is measured in accordance with ASTM D792, Method B. The result is recorded in g/cc.

Melt flow (MF) (I2) in g/10 min for propylene-based polymers and ethylene-based polymers is measured using ASTM D-1238-04 (190° C./2.16 kg). Melt flow (MF) (I10) in g/10 min for propylene-based polymers and ethylene-based polymers is measured using ASTM D-1238-04 (190° C./10.0 kg).

Haze is measured in accordance with ASTM D1003.

Clarity (Zebedee) is measured in accordance with ASTM D1746.

The predicted half-life of a sulfonyl azide anhydride is measured using DSC by scanning the sulfonyl azide anhydride at various heating rates. The DSC data collected is utilized to compute the kinetic parameters using AKTS-Thermokinetics Software (available from Advanced Kinetics and Technology Solutions AG). Applying the computed kinetic parameters, the reaction progress for a specific temperature profile is predicted. Subsequently, the predicted half-life of the sulfonyl azide anhydride is obtained from the reaction progress vs. time plot at a given temperature. The same procedure is utilized for a blend of the sulfonyl azide anhydride in ENGAGE™ 8400 (an ethylene/octene copolymer available from The Dow Chemical Company) at a concentration of 2.07 wt. % of the sulfonyl azide anhydride. The predicted half-life is measured in seconds (sec.).

Limiting impact energy is determined using the German Federal Institute for Testing Materials (BAM) Fall Hammer Test. Impact energy is imparted to a 40 mm$^3$ sample of the sulfonyl azide anhydride by a falling weight using the BAM Fall Hammer apparatus. The limiting impact energy is determined as the lowest energy at which a flash, flame or explosion is observed. The test assesses the sensitivity of the sulfonyl azide anhydride to drop-weight impact. The method yields quantitative results in the form of limiting impact energy. The testing is carried out at Chilworth Technology Inc., now part of DEKRA Insight. The limiting impact energy is measured in Joules (J).

Differential Scanning calorimetry (DSC) is used to measure crystallinity in the polymer (e.g., ethylene-based (PE) polymer). About 5 to 8 mg of polymer sample is weighed and placed in a DSC pan. The lid is crimped on the pan to ensure a closed atmosphere. The sample pan is placed in a DSC cell, and then heated, at a rate of approximately 10° C./min, to a temperature of 180° C. for PE (230° C. for polypropylene). The sample is kept at this temperature for three minutes. Then the sample is cooled at a rate of 10° C./min to −60° C. for PE (−40° C. for PP), and kept isothermally at that temperature for three minutes. The sample is next heated at a rate of 10° C./min, until complete melting (second heat). The percent crystallinity is calculated by dividing the heat of fusion ($H_f$), determined from the second heat curve, by a theoretical heat of fusion of 292 J/g for PE (165 J/g, for PP), and multiplying this quantity by 100 (for example, % cryst.=($H_f$/292 J/g)×100 (for PE)). Unless otherwise stated, melting point(s) ($T_m$) of each polymer is determined from the second heat curve (peak Tm), and the crystallization temperature ($T_a$) is determined from the first cooling curve (peak Tc).

Small Scale Sample Preparation for Mini-Adhesion Testing

Mini-adhesion test samples are prepared by compression molding to obtain adhesion data on the sample modified polyolefins using a polyamide film as substrate (ULTRAMID C33-01L). A special polyamide test film was prepared consisting of a five layer structure DOWLEX™ 2045G/AMPLIFY™ TY 1353/Polyamide (ULTRAMID™ C33-01L)/DOWLEX™ 2045G/DOWLEX™ 2045G with 30/10/20/10/30 wt % for each layer, respectively.

The test sample preparation procedure is described below to determine the adhesion force between the modified polyolefin and a polyamide film. This test is a simplified method for determining the adhesion in a commercial processing procedure:

1a) A tie layer film (Example) is prepared by compression molding ~7 to 10 g of the synthesized SAA-g-PE between 125 micron Mylar sheet liners using the following program on a Pasadena Hydraulics Inc. (PHI) 4 platen press, Model: 30U1212S4JCS-N-MS, with all zones set to 340° F. (~170° C.):

5 minutes (min) at 1,000 lbs (453.592 kg) force on the "low" pressure setting ("melt");
7 min. at 30,000 lbs (13,601.771 kg) force on the "high" pressure setting ("cure"); and
10 min. at 30,000 lbs (13,601.771 kg) force on the "high" pressure setting with the water cooling active.

1b) Tie layer film (Control) preparation using MAH-g-PE-control sample synthesized via free radical grafting, is performed by compression molding 7 g to 10 g of material between Teflon coated aluminum foil and following the same program as described above on Pasadena Hydraulics Inc. (PHI) 4 platen press.

2) Two approximately 200 mm by 200 mm squares of the polyamide test films are cut. The polyethylene cover sheets from the polyamide films are delaminated and the polyamide test films are positioned in such a way that the polyamide portions are against the tie layer film. The DOWLEX™ 2045G layer can be delaminated from the polyamide surface since there is not a tie layer present.

3) The tie layer film, cut to a 150 mm by 150 mm square, is positioned between the delaminated polyamide test films.

4) A ~25 mm wide, 50 micron Teflon strip is placed as spacer along one edge of the tie layer between the polyamide films.

5) The prepared assembly is placed between two Teflon sheets (two Teflon coated aluminum foil sheets for the assemblies prepared using MAH-g-PE control sample and un-processed DOWLEX™ 2045G control sample) and compression molded at 320° F. (~160° C.), 6,000 lbs (2,721.554 kg) force for 3 hours in the PHI press.

6) After three hours the cooling is activated while maintaining 6,000 lbs (2,721.554 kg) force. Sample assemblies are removed from the press once platen temperature is 80° C., and allowed to cool to room temperature.

T-Peel Test Performed on Small Scale Compression Molded Samples of the Type: Polyamide/SAA-g-PE/Polyamide For T-peel test, the small scale compression molded samples described above are prepared by separating the layers once the spacer Teflon strip is removed so one side has tie layer-polyamide and the other is only polyamide. Subsequently, the films are cut into 25 mm wide strips and about 150 mm long using a JDC "Precision Sample Cutter," model JDC 1-10. Cuts are made with the separated edges at the "top" of the strips. Adhesion data is collected using a TA. XT. Plus Texture Analyzer, Textures Technology Corp., Stable Micro Systems, with Exponent Stable Micro Systems Vers. 4,0,13,0, Formula One & First Impression (Visual Components, Inc.) software. Instrument is calibrated for probe height and force prior to running tests.

The T-peel test procedure is described below:

1) Peel tabs are initiated in a region where the spacer Teflon strip ended. Separation "interface" is adjusted to get a straight line across the strip at 90° to the strip's edges.

2) The polyamide-tie layer side is placed in the lower "stationary" clamp of the TA XT. Plus Texture Analyzer. Polyamide only layer is secured in the upper "traveling" clamp.

3) The sample is peeled at 250 mm per minute jaw speed, total displacement set to 125 mm to allow more than one test to be run on a strip if desired. The mean adhesion force per sample strip is recorded as a function of displacement.

4) The resulting Peel Strength value is reported in newtons (N) per meter (m) or N/m and is generally an average of three to five independent readings.

Grafting Levels of Maleic Anhydride (MAH) Determination

The grafting levels of MAH are determined via manual colorimetric titration. The sample (7-10 g for the Control Sample and Examples A-B) (10 g for scale-up Example C) is purified via a precipitation of a hot toluene polymer solution (350 mL) into acetone (1 L). The MAH-grafted polymer is collected by filtration, washed with acetone (2×300 mL) and the polymer sample is dried in a vacuum oven at 80° C., overnight. Prior to the titration experiment, the purified polymer is dried in a nitrogen purged vacuum oven at 130° C. for one hour. Subsequently, 1 gram of the dried sample is dissolved in hot xylenes. The sample is titrated with 0.025 N tetrabutylammonium hydroxide (0.020 N for scale-up Example C) in 50/50 methanol/toluene using bromothymol blue indicator to a constant blue color endpoint. The sample is titrated three times and the results are averaged.

By way of example, and not limitation, some embodiments of the present disclosure will now be described in detail in the following Examples.

EXAMPLES

1. Materials

Materials used in examples are provided in Table 2 below.

TABLE 2

| Material/Description | Properties | Source |
|---|---|---|
| DOWLEX ™ 2045G (ethylene/1-octene copolymer) - LLDPE | Melt flow (I2)(190° C./2.16 kg) = 1.0 g/10 min, Density = 0.92 g/cc, Melting point = 122° C. | Dow |
| Maleic anhydride | Melting point = 52-54° C., Relative density = 1.48 g/cc. | Aldrich |

TABLE 2-continued

| Material/Description | Properties | Source |
|---|---|---|
| 5-(azidosulfonyl)endo-cis-bicyclo[2.2.1]heptane-2,3-dicarboxylic anhydride | Structure (1a) (see Table 1A above) Limiting impact energy (BAM Fall Hammer Test): >60 J. Predicted half-life (neat) at 210° C. (DSC, isoconversional analysis) = 54.6 sec. Predicted half-life (in ENGAGE ™ 8400 blend at a 2.07 wt % concentration of 5-(azidosulfonyl)endo-cis-bicyclo[2.2.1]heptane-2,3-dicarboxylic anhydride) at 210° C. (DSC, isoconversional analysis) = 88.9 sec. | Dow |
| 3-(2,5-dioxotetrahydrofuran-3-yl)-2-methylpropane-1-sulfonyl azide | Structure (1b) (see Table 1A above) | Dow |
| Luperox 101 (2,5 dimethyl 2,5-di-t-butylperoxy Hexane), 90% | Density = 0.877 g/cc (25° C.). | Aldrich |
| AMPLIFY ™ TY 1353 | Density = 0.92 g/cc, MAH graft level = low, Melt flow (190° C./2.16 Kg) = 2.1 g/10 min. | Dow |
| Nylon (Ultramid C33-01L) Polyamide PA 6/66 | Melting point = 196° C., Density = 1.12 g/cc. | BASF |
| IRGANOX ™ 1010 (Pentaerythritol Tetrakis(3-(3,5-di-tert-butyl-4-hydroxyphenyl)propionate)) | Melting point range = 110-125° C., Specific gravity = 1.15 g/cc (20° C.). | Ciba |
| EVAL ™ H171B (EVOH copolymer) | Density = 1.17 g/cc, Melting point = 172° C., Melt flow rate (190° C./2.16 Kg) = 1.7 g/10 min. | Kuraray |
| DJM-1810H (ethylene/1-hexene copolymer) - LLDPE | Melt flow (I2) (190° C./2.16 Kg) = 1.0 g/10 min, Density = 0.918 g/cc, Melting point = 124° C. | Dow (internal feed stock) |

2. Control Sample—Preparation of Free Radical MAH-g-PE

Procedure for grafting reaction of maleic anhydride onto polyethylene in pellet form performed in a Haake mixer: Polyethylene pellets (DOWLEX 2045G) (44.82 g control, 44.87 g CS-A) are weighed into a 4 ounce wide mouth polypropylene bottle with matching cap. The grafting reaction is performed using a rebuilt Thermo Scientific Haake Polylab, Model 557-9301, with a Rheomix 600p, Model 557-1302, Hastelloy bowl and matching roller rotors/paddles installed and connected to a Gateway Windows 8 laptop computer. Control of the motor system is from a SEW Eurodrive MDX61B motor controller with MOVITOOLS—MotionStudio, vers. 5.70, (5.7.0.2) software. An external box with Watlow Ez-zone units installed is used to set plate/bowl temperatures and high temperature limits. A Graphtec midi logger GL220 with GL220 820APS application software is used for data collection. The temperature at the Haake instrument is set to 180° C. and the system is allowed to equilibrate. The polyethylene pellets are added to the Haake instrument and fluxed at a screw rpm of 30 for 2 min. The desired amount of maleic anhydride (N/A for control, 0.40 wt %, 0.181 g for CS-A) is added to the instrument via a dose bag (0.183 g for control, 0.130 g for CS-A), the screw rpm is increased to 80 and the mixture is fluxed for 2 min. Subsequently, Luperox 101 (N/A for control, 0.11 wt %, 57 µL CS-A) is added via syringe and the mixture is fluxed for an additional 6 min. The Haake instrument is stopped and the MAH-g-PE polymer is removed from the mixer while hot. Table 3 shows the characterization results from the synthesized control MAH-grafted ethylene-based polymer (MAH-g-PE). The samples are tested for MAH grafting levels. Adhesion samples are prepared in accordance with the mini-adhesion test sample preparation described above and tested for peel strength in accordance with the T-Peel test described above.

TABLE 3

Characterization of MAH-g-PE Control Polymers.

| Run # | wt % MAH (titration)[a] | GE (%)[b] | $M_w$[c] | $M_n$[c] | PDI[c] | I2[d] | I10[d] | Ratio I10/I2 | Peel strength[e] (N/m) |
|---|---|---|---|---|---|---|---|---|---|
| DOWLEX 2045G control processed at 180° C. | NA | NA | 103,590 | 26,585 | 3.90 | 0.22 | 5.29 | 24.0 | ND |
| Comparative Sample A (CS-A) | 0.26 ± 0.03 | 65 ± 09 | 98,435 | 21,315 | 4.62 | 0.13 | 3.14 | 24.1 | 657 ± 0161 |

[a]Average of three measurements.
[e]Average of four measurements.
ND = not detected.
[b]GE = grafting efficiency = ((wt % MAH grafted)/(Equivalent wt % MAH added to the reaction))*100.
[c]High temperature GPC data is obtained on crude samples (one measurement).
[d]I2 and I10 data obtained on crude samples using a Melt Flow Jr. instrument from CEAST, which follows the ASTM D 1238 method (1 measurement).

3. Example A—Preparation of Bicyclo SAA-g-PE

Procedure for grafting reaction of 5-(azidosulfonyl)endo-cis-bicyclo[2.2.1]heptane-2,3-dicarboxylic anhydride onto polyethylene in pellet form performed in a Haake mixer: Polyethylene pellets (DOWLEX 2045G) are weighed into 125 mL wide mouth glass jar with a Teflon lined cap. The desired weight of mineral oil is added. The contents of the jar are sealed and placed within a secondary polyethylene jug, containing a pad with absorbent material. The blend contents are tumbled on a roller for 2 hours. After 2 hours, the desired amount of Irganox 1010 is added, followed by 5-(azidosulfonyl)endo-cis-bicyclo[2.2.1]heptane-2,3-dicarboxylic anhydride. The contents of the jar are sealed and placed within a secondary polyethylene jug, containing a pad with absorbent material. The blend contents are tumbled on a roller overnight to uniformly distribute the azide compound onto the polyethylene pellets. The next day, the grafting reaction is performed using a rebuilt Thermo Scientific Haake Polylab, Model 557-9301, with a Rheomix 600p, Model 557-1302, Hastelloy bowl and matching roller rotors/paddles installed and connected to a Gateway Windows 8 laptop computer. Control of the motor system is from a SEW Eurodrive MDX61B motor controller with MOVI-TOOLS—Motion Studio, vers. 5.70, (5.7.0.2) software. An external box with Watlow EZ-zone units installed is used to set plate/bowl temperatures and high temperature limits. A Graphtec midi logger GL220 with GL220 820APS application software is used for data collection. The temperature at the Haake instrument is set to 200° C. and the system is allowed to equilibrate. The pre-mixed polyethylene pellets with 5-(azidosulfonyl)endo-cis-bicyclo[2.2.1]heptane-2,3-dicarboxylic anhydride are added to the Haake, and the mixture is fluxed for 5 min with a screw rpm=80. The Haake instrument is subsequently stopped and the bicyclo SAA-g-PE polymer is removed from the mixer while hot. Table 4 shows the material quantities used in the grafting experiments, and Table 5 shows the characterization results from the synthesized bicyclo SAA-g-PE polymers. The samples are tested for MAH grafting levels. Adhesion samples are prepared in accordance with the mini-adhesion test sample preparation described above and tested for peel strength in accordance with the T-Peel test described above.

TABLE 4

Material quantities used in the grafting reactions of 5-(azidosulfonyl)endo-cis-bicyclo[2.2.1]heptane-2,3-dicarboxylic anhydride onto polyethylene in pellets.

| Example # | DOWLEX 2045G (g) | Mineral oil (wt %, g) | Irganox 1010 (wt %, g) | 5-(azidosulfonyl)endo-cis-bicyclo[2.2.1]heptane-2,3-dicarboxylic anhydride (wt %, g) | Equivalent wt % MAH | Jar residue (g)[a] |
|---|---|---|---|---|---|---|
| DOWLEX 2045G control processed at 200° C. | 45.001 | NA | NA | NA | NA | — |
| Example 1 | 45.004 | 0.198, 0.089 | 0.0494, 0.0224 | 0.532, 0.241 | 0.192 | 0.059 |
| Example 2 | 44.999 | 0.394, 0.180 | 0.0486, 0.0222 | 1.055, 0.482 | 0.381 | 0.046 |
| Example 3 | 44.998 | 0.777, 0.359 | 0.0483, 0.0224 | 2.080, 0.964 | 0.751 | 0.012 |
| Example 4 | 45.002 | 1.148, 0.539 | 0.0474, 0.0223 | 3.077, 1.446 | 1.11 | 0.026 |

General grafting conditions: T = 200° C., rpm = 80, time = 5 min. DOWLEX 2045G (pellet).
[a]Residue left in the jars after transferring the mixture of PE and aliphatic sulfonyl azide anhydride molecule into the Haake instrument.

TABLE 5

Characterization of bicyclo SAA-g-PE Polymers.

| Run# | wt % MAH (tritration)[a] | GE (%)[b] | $M_w$[c] | $M_n$[c] | PDI[c] | I2[d] | I10[d] | Ratio I10/I2 | Peel strength (N/m) |
|---|---|---|---|---|---|---|---|---|---|
| DOWLEX 2045G control processed at 200° C. | NA | NA | 101,300 | 17,725 | 5.7 | 0.78 | 8.04 | 10.3 | 5.9 ± 3.3[e] |
| Example 1 | 0.12 ± 0.02 | 61 ± 8 | 114,585 | 24,385 | 4.7 | 0.30 | 4.69 | 15.6 | 548 ± 76[f] |
| Example 2 | 0.25 ± 0.03 | 66 ± 8 | 115,675 | 26,415 | 4.4 | 0.48 | 5.43 | 11.3 | 1138 ± 168[f] |
| Example 3 | 0.35 ± 0.02 | 46 ± 3 | 125,755 | 27,020 | 4.6 | 0.38 | 4.62 | 12.2 | |
| Example 4 | 0.38 ± 0.03 | 34 ± 2 | 123,420 | 24,075 | 5.1 | 0.34 | 4.53 | 13.3 | |

[a]Average of three measurements.

[b]GE = grafting efficiency = ((wt % MAH grafted)/(Equivalent wt % MAH added to the reaction))*100.

[c]High temperature GPC data is obtained on crude samples (one measurement).

[d]I2 and I10 data obtained on crude samples using a Melt Flow Jr. instrument from CEAST, which follows the ASTM D 1238 method (1 measurement).

[e]Peel strength obtained on un-processed DOWLEX 2045G sample (average of three measurements).

[f]Average of three measurements.

4. Example B—Preparation of Branched SAA-g-PE

Procedure for grafting reaction of 3-(2,5-dioxotetrahydrofuran-3-yl)-2-methylpropane-1-sulfonyl azide onto polyethylene in pellet form performed in a Haake mixer: Polyethylene pellets (DOWLEX 2045G) are weighed into 125 mL wide mouth glass jar with a Teflon lined cap. For the DOWLEX 2045G control sample, a 4 ounce polypropylene-based container is used. The desired amount of 3-(2,5-dioxotetrahydrofuran-3-yl)-2-methylpropane-1-sulfonyl azide is weighed into a 10 mL vial. Dichloromethane is added to the vial containing the aliphatic sulfonyl azide molecule. The solution is transferred to the 125 mL wide mouth glass jar containing the polyethylene pellets. The vial is rinsed with dichloromethane (3 mL) to ensure complete transfer of the solution containing the aliphatic sulfonyl azide molecule. The contents of the jar are sealed, shaken, and placed within a secondary polyethylene jug, containing a pad with absorbent material. The blend contents are tumbled on a roller for 2 hours. After two hours, the desired amount of Irganox 1010 is added. The contents of the jar are sealed, shaken, and placed within a secondary polyethylene jug, containing a pad with absorbent material. The blend contents are tumbled on a roller overnight to uniformly distribute the azide compound onto the polyethylene pellets. The next day, the jar is transferred to a heated vacuum oven set to 40° C. to remove the dichloromethane solvent overnight. The drying step is repeated for another 5 hours on a second day due to a trace amount of dichloromethane determined to be present in the mixture. Following complete drying of the mixture, the grafting reaction is performed using a rebuilt Thermo Scientific Haake Polylab, Model 557-9301, with a Rheomix 600p, Model 557-1302, Hastelloy bowl and matching roller rotors/paddles installed and connected to a Gateway Windows 8 laptop computer. Control of the motor system is from a SEW Eurodrive MDX61B motor controller with MOVITOOLS—MotionStudio, vers. 5.70, (5.7.0.2) software. An external box with Watlow EZ-zone units installed is used to set plate/bowl temperatures and high temperature limits. A Graphtec midi logger GL220 with GL220 820APS application software is used for data collection. The temperature at the Haake instrument is set to 200° C. and the system is allowed to equilibrate. The pre-mixed polyethylene pellets with 3-(2,5-dioxotetrahydrofuran-3-yl)-2-methylpropane-1-sulfonyl azide are added to the Haake, and the mixture is fluxed for 5 min with a screw rpm=80. The Haake instrument is subsequently stopped and the branched SAA-g-PE polymer is removed from the mixer while hot. Table 6 shows the material quantities used in the grafting experiments, and Table 7 shows the characterization results from the synthesized branched SAA-g-PE polymers. Adhesion samples are prepared in accordance with the mini-adhesion test sample preparation described above and tested for peel strength in accordance with the T-Peel test described above.

TABLE 6

Material quantities used in the grafting reactions of 3-(2,5-dioxotetrahydrofuran-3-yl)-2-methylpropane-1-sulfonyl azide onto polyethylene in pellets.

| Example # | DOWLEX 2045G (g) | Irganox 1010 (wt %, g) | 3-(2,5-dioxotetrahydrofuran-3-yl)-2-methylpropane-1-sulfonyl azide (wt %, g) | Equivalent wt % MAH | Jar residue (g)[a] |
|---|---|---|---|---|---|
| DOWLEX 2045G control processed at 200° C. | 49.995 | NA | NA | NA | — |
| Example 5 | 45.000 | 0.0504, 0.0228 | 0.512, 0.2317 | 0.192 | 0.008 |

General grafting conditions: T = 200° C., rpm = 80, time = 5 min. DOWLEX 2045G (pellet).
[a]Residue left in the jars after transferring the mixture of PE and aliphatic sulfonyl azide anhydride molecule into the Haake instrument.

TABLE 7

Characterization of branched SAA-g-PE Polymers.

| Run# | wt % MAH (titration)[a] | GE (%)[b] | $M_w$[c] | $M_n$[c] | PDI[c] | I2[d] | I10[d] | Ratio I10/I2 | Peel strength (N/m) |
|---|---|---|---|---|---|---|---|---|---|
| DOWLEX 2045G control processed at 200° C. | NA | NA | 107,465 | 25,810 | 4.2 | 0.37 | 5.29 | 14.3 | 5.9 ± 3.3[e] |
| Example 5 | 0.12 ± 0.005 | 61 ± 3 | 113,855 | 28,235 | 4.0 | 0.46 | 5.94 | 12.9 | 956 ± 121[f] |

[a]Average of three measurements.
[b]GE = grafting efficiency = ((wt % MAH grafted)/(Equivalent wt % MAH added to the reaction))*100.
[c]High temperature GP data is obtained on crude samples (one measurement).
[d]I2 and I10 data obtained on crude samples using a Melt Flow Jr. instrument from CEAST, which follows the ASTM D 1238 method (1 measurement).
[e]Peel strength obtained on un-processed DOWLEX 2045G sample (average of three measurements).
[f]Average of three measurements.

5. Scale-Up Example C—Preparation of Bicyclo SAA-g-PE

Scale-up grafting reaction of 5-(azidosulfonyl)endo-cis-bicyclo[2.2.1]heptane-2,3-dicarboxylic anhydride onto polyethylene in granular form (2.5 kg) performed in a Leistritz 18 mm Extruder (Twin-Screw): Polyethylene in the granular form (DJM-1810H ethylene/1-hexene copolymer) is weighed into 5 separate 1/2 gallon wide mouth glass jars with Teflon lined caps. The desired amount of 5-(azidosulfonyl)endo-cis-bicyclo[2.2.1]heptane-2,3-dicarboxylic anhydride is weighed into 5 separate 20 mL glass vials inside a fume hood. The desired amount of Irganox 1010 is weighed into 5 separate plastic weigh boats. Into the 5 separate 1/2 gallon wide mouth glass jars with polyethylene is transferred the desired amounts of Irganox 1010 and 5-(azidosulfonyl)endo-cis-bicyclo[2.2.1]heptane-2,3-dicarboxylic anhydride compound. Subsequently, to the 5 separate 1/2 gallon jars are sealed, shaken, and the contents are tumbled on a roller overnight to uniformly distribute the azide/Irganox 1010 mixture into the granular polyethylene. The next day, the azide/polyethylene dry blend is ready to be run in an extruder. The extruder is purged the day before the run for 2 hours and the day of the run for 1 hour with granular polyethylene (DJM-1810H), gas-phase resin at the desired temperature profile: set temp at Zone 1=140° C., set temp at Zone 2=200° C., set temp at Zone 3 to Zone 8 (die)=230° C. with a screw rpm=200 and the flow rate setting is adjusted to be 0.38 kg/h to obtain a residence time of approximately 4.10 min. The additional use of a low flow of nitrogen cover gas as plumbed to the feed throat is utilized to minimize oxidation of the base resin. Subsequently, 1,500 grams (3 of the 5 jars) of the pre-mixed granular polyethylene with 5-(azidosulfonyl)endo-cis-bicyclo[2.2.1]heptane-2,3-dicarboxylic anhydride and Irganox 1010 are loaded into the feed hopper of the K-Tron KCL24-KT20 solid feeder inside a fume hood. The pre-mixed granular polyethylene and 5-(azidosulfonyl)endo-cis-bicyclo[2.2.1]heptane-2,3-dicarboxylic anhydride are run through the extruder for 20 min before polymer collection started. After the extruder is stabilized, the extrudate is collected continuously as a single strand that is directed to a water-bath-pelletizer system to draw/cool and pelletize the polymer strand. The water bath is cooled with a chiller using an antifreeze coolant (propylene glycol formula mixed with water). Once the level of polyethylene and 5-(azidosulfonyl)endo-cis-bicyclo[2.2.1]heptane-2,3-dicarboxylic anhydride gets low, the remaining 2 jars of the pre-mixed granular polyethylene with 5-(azidosulfonyl)endo-cis-bicyclo[2.2.1]heptane-2,3-dicarboxylic anhydride and Irganox 1010 is added-500 grams is added first, and then the last 500 grams is placed in the solid feeder once the mixture gets low in the feeder. It is noticed that when the level of the pre-mixed granular polyethylene with 5-(azidosulfonyl)endo-cis-bicyclo[2.2.1]heptane-2,3-dicarboxylic anhydride and Irganox 1010 gets low in the solid feeder, the polymer strand comes out of the extruder with a darker color. After the run is completed, the extruder is purged with plain granular polyethylene (DJM-1810H) resin for 30 minutes. The next day, the extruder is further purged with plain granular polyethylene (DJM-1810H) resin for 50 minutes, followed by granular polyethylene (DJM-1810H) resin and 300 mL water (added via the feed throat) for 52 minutes, followed by plain granular polyethylene (DJM-1810H) gas-phase resin for 1 hour. The extruder is purged with polyethylene and water at the desired temperature profile: set temp at Zone 1=140° C., set temp at Zone 2 to Zone 8 (die)=190° C. with a screw rpm=15-20. Table 8 shows the material quantities used in the scale-up run, and Table 9 shows the characterization results from the synthesized bicyclo SAA-g-PE (sample that is collected at time=3.5 hours (h)). The total amount of polymer collected is 2571 g.

The samples are tested for MAH grafting levels in accordance with the procedure described above.

The material quantities specified in Table 8 are combined and run in the extruder to prepare bicyclo SAA-g-PE (scale-up or Example 6). A sample is collected at time=3.5 hours for testing shown in Table 9.

TABLE 8

Material quantities used in the scale-up grafting reaction of 5-(azidosulfonyl)endo-cis-bicyclo[2.2.1]heptane-2,3-dicarboxylic anhydride onto polyethylene in granular form.

| Run# | DJM-1810H (g) | Irganox 1010 (wt %, g) | 5-(azidosulfonyl)endo-cis-bicyclo[2.2.1]heptane-2,3-dicarboxylic anhydride (wt %, g) | Equivalent wt % MAH | Jar residue (g)[a] |
|---|---|---|---|---|---|
| Gas-phase PE resin (control) | Extruded sample from instrument purge | NA | NA | NA | NA |
| Example 6 (Jar # 1, ½ gallon) | 550.01 | 0.0497, 0.2750 | 0.4969, 2.747 | 0.179 | 3.06 |
| Example 6 (Jar # 2, ½ gallon) | 550.00 | 0.0497, 0.2748 | 0.4972, 2.749 | 0.1179 | 1.53 |
| Example 6 (Jar # 3, ½ gallon) | 550.00 | 0.0498, 0.2754 | 0.4972, 2.749 | 0.179 | 5.04 |
| Example 6 (Jar # 4, ½ gallon) | 550.01 | 0.0496, 0.2745 | 0.4979, 2.753 | 0.179 | 5.74 |
| Example 6 (Jar # 5, ½ gallon) | 550.01 | 0.0498, 0.2752 | 0.4971, 2.749 | 0.179 | 9.88 |

Temperature profile: Zone 1 temp = 140° C., Zone 2 temp = 200° C., Zone 3 to Zone 8 (die) temp = 230° C. rpm = 200. DJM-1810H gas-phase PE resin (granular). Flow rate = 0.38 kg/h.
[a]Residue left in the jars after transferring the mixture of PE and 5-(azidosulfonyl)endo-cis-bicyclo[2.2.1]heptane-2,3-dicarboxylic anhydride to the solid feeder.

TABLE 9

Characterization of scale-up bicyclo SAA-g-PE Polymer.

| Run# | wt % MAH (titration)[a] | GE (%)[b] | $M_w$[c] | $M_n$[c] | PDI[c] | I2[d] | I10[d] | Ratio I10/I2 |
|---|---|---|---|---|---|---|---|---|
| Gas-phase PE resin (control) processed at 230° C. | NA | NA | 122,265 | 23,280 | 5.2 | 0.59 | 6.60 | 11.18 |
| Example 6 (combined examples from Example 6 Jars #1-5, collected at time = 3.5 h) | 0.14 ± 0.006 | 80 ± 3 | 131,300 | 26,040 | 5.0 | 0.57 | 5.58 | 9.78 |

[a]Average of three measurements.
[b]GE = grafting efficiency = ((wt % MAH grafted)/(Equivalent wt % MAH added to the reaction))*100.
[c]High temperature GPC data is obtained on crude samples (one measurement).
[d]I2 and I10 data obtained on crude samples using a Melt Flow Jr. instrument from CEAST, which follows the ASTM D1238 method (1 measurement).

6. Multilayer Film

Four film samples are prepared using the bicyclo SAA-g-PE from Example 6 and the layer compositions are outlined in Table 10.

The prepared film samples are collected and evaluated for adhesion strength without any further heat treatment. Adhesion test strips prepared by the following procedure.

Test strips are prepared from the 5 layer blown film, which is cut using a 2.54 cm×15.24 cm punch die in machine direction. Two strips are placed between a thermal sealer with jaws set to 140° C. and the strips are exposed to force for approximately 0.3 seconds approximately 2.54 cm from one end. This action effectively seals the two strips together at the point of impact from the jaws. The tabs are pulled apart by hand and this forces a separation at the interface between the nylon (or EVOH copolymer) and the tie layer. The freshly separated parts are then placed into the jaws of an Instron and pulled apart at a rate of 5.08 cm/min. FIG. 1 is a schematic representation of the adhesion force test. For 5 independent samples, the average force needed to initiate delamination is recorded in Table 10. The force needed to induce delamination for the azide samples are similar to the comparative samples.

TABLE 10

Blown Film Composition.

| Layer | Layer weight % | Run #1 (control) | Example 7 | Run #3 (control) | Example 8 |
|---|---|---|---|---|---|
| A | 30 | DOWLEX 2045G | DOWLEX 2045G | DOWLEX 2045G | DOWLEX 2045G |
| B | 10 | AMPLIFY TY 1353 | bicyclo SAA-g-PE* | AMPLIFY TY 1353 | bicyclo SAA-g-PE* |
| C | 20 | Nylon[◊] | Nylon[◊] | EVOH copolymer[#] | EVOH copolymer[#] |
| D | 10 | AMPLIFY TY 1353 | bicyclo SAA-g-PE* | AMPLIFY TY 1353 | bicyclo SAA-g-PE* |
| E | 30 | DOWLEX 2045G | DOWLEX 2045G | DOWLEX 2045G | DOWLEX 2045G |
| Comments | | Total film thickness = 101.6 micron (4.0 mil) | Established run parameters using commercial tie layer | Replaced AMPLIFY TY 1353 with bicyclo SAA-g-PE in layers B &D with no adjustments made to rate or temp. | Established run parameters using commercial tie layer | Replaced AMPLIFY TY 1353 with bicyclo SAA-g-PE in layers B & D with no adjustments made to rate or temp. |
| Peel Strength (average of five readings) | N/m | 541 | 683 | 547 | 568 |
| Std. Dev. Peel Strength | N/m | 252 | 14 | 16 | 18 |

*Bicyclo SAA-g-PE of Example 6.
[◊]Nylon is Ultramid C33-01L.
[#]EVOH copolymer is EVAL ™ H171B.

The optical properties are also evaluated for the films. The data is shown Table 11 below.

TABLE 11

|  | Nylon Film | | EVOH Copolymer Film | |
| --- | --- | --- | --- | --- |
|  | Run #1 (control) | Example 7 (bicyclo SAA-g-PE) | Run #3 (control) | Example 8 (bicyclo SAA-g-PE) |
| Haze (%)* | 12.9 | 12.7 | 16.9 | 16.3 |
| Clarity (%) Zebedee* | 62.6 | 59.04 | 39.7 | 15.02 |

*Average of five readings.

Applicant discovered a multilayer film is produced where interlayer adhesion using SAA-g-PE as the tie layer surprisingly has the same or better adhesion properties as conventional MAH-g-PE prepared by a free radical process. The present SAA-g-PE tie layer experiences little, or no, undesired crosslinking. Additionally, multilayer film produced with the present SAA-g-PE generally exhibits optical properties such as haze and clarity equal to, or better than, multilayer film made with conventional MAH-g-PE prepared by a free radical process. These results confirm that sulfonamide aliphatic anhydride-graft-olefin-based polymer (and branched SAA-g-PE and bicyclo SAA-g-PE in particular) is an effective tie layer that advantageously avoids the negative processing effects of free radical MAH-grafted-polyolefin.

It is specifically intended that the present disclosure not be limited to the embodiments and illustrations contained herein, but include modified forms of those embodiments including portions of the embodiments and combinations of elements of different embodiments as come within the scope of the following claims.

We claim:

1. A composition comprising a sulfonamide aliphatic anhydride grafted olefin-based polymer (SAA-g-PO) having a Structure (2):

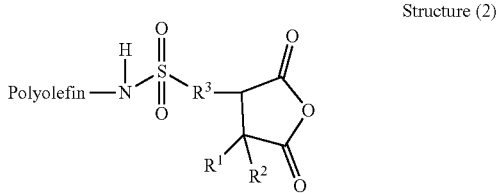

Structure (2)

wherein $R^1$, $R^2$, and $R^3$ may be the same or different; and
$R^1$, $R^2$, and $R^3$ each is independently selected from a substituted $C_1$-$C_{40}$ hydrocarbonyl group, an unsubstituted $C_1$-$C_{40}$ hydrocarbonyl group, $Si(R^C)_3$, $OR^C$, $R^CC(O)O$—, $R^COC(O)$—, $R^CC(O)N(R)$—, $(R^C)_2NC(O)$—, a halogen atom, and a hydrogen atom, wherein $R^C$ is a $C_1$-$C_{30}$ hydrocarbonyl group;
with the proviso that at least one of $R^1$, $R^2$, and $R^3$ is selected from a substituted $C_1$-$C_{40}$ hydrocarbonyl group or an unsubstituted $C_1$-$C_{40}$ hydrocarbonyl group, and $R^3$ is not a halogen atom or hydrogen atom.

2. The composition of claim 1, wherein the $R^1$ and the $R^3$ groups form an unsubstituted $C_3$-$C_{50}$ hydrocarbonyl group ring structure.

3. The composition of claim 1, wherein
$R^2$ is hydrogen; and
the $R^1$ and the $R^3$ groups form an unsubstituted $C_3$-$C_8$ hydrocarbonyl group ring structure.

4. The composition of claim 1, wherein the SAA-g-PO is a 5-(sulfonamide)endo-cis-bicyclo[2.2.1]heptane-2,3-dicarboxylic anhydride grafted polyethylene having a Structure (2a):

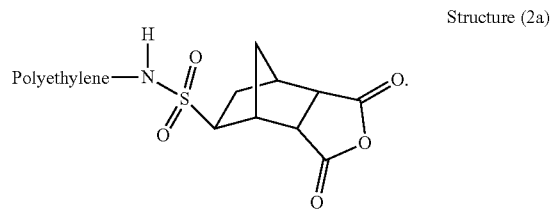

Structure (2a)

5. The composition of claim 1, wherein $R^1$ and $R^2$ each is hydrogen; and $R^3$ is an unsubstituted $C_1$-$C_{12}$ hydrocarbonyl group.

6. The composition of claim 5, wherein the sulfonamide aliphatic anhydride is sulfonamide 3-(2,5-dioxotetrahydrofuran-3-yl)-2-methylpropane grafted polyolefin.

7. The composition of claim 5, wherein the SAA-g-PO is a sulfonamide 3-(2,5-dioxotetrahydrofuran-3-yl)-2-methylpropane grafted polyethylene having a Structure (2b):

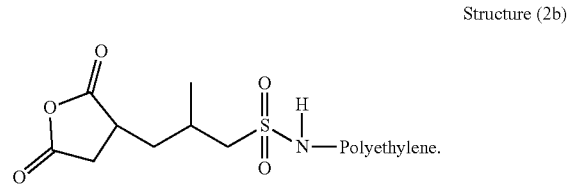

Structure (2b)

8. The composition of claim 1, wherein the olefin-based polymer is an ethylene-based polymer.

9. A multilayer film comprising:
a layer (A) comprising an olefin-based polymer;
a layer (B) that is a tie layer comprising a sulfonamide aliphatic anhydride grafted olefin-based polymer (SAA-g-PO); and
a layer (C) comprising a polar component.

10. The multilayer film of claim 9, wherein the SAA-g-PO has a Structure (2):

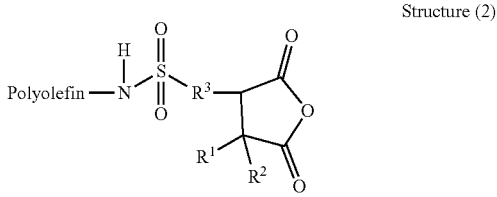

Structure (2)

wherein $R^1$, $R^2$, and $R^3$ may be the same or different;
wherein $R^1$, $R^2$, and $R^3$ may be the same or different; and
$R^1$, $R^2$, and $R^3$ each is independently selected from a substituted $C_1$-$C_{40}$ hydrocarbonyl group, an unsubstituted $C_1$-$C_{40}$ hydrocarbonyl group, $Si(R^C)_3$, $OR^C$, $R^CC(O)O$—, $R^COC(O)$—, $R^CC(O)N(R)$—, $(R^C)_2NC(O)$—, a halogen atom, and a hydrogen atom, wherein $R^C$ is a $C_1$-$C_{30}$ hydrocarbonyl group;

with the proviso that at least one of $R^1$, $R^2$, and $R^3$ is selected from a substituted $C_1$-$C_{40}$ hydrocarbonyl group or an unsubstituted $C_1$-$C_{40}$ hydrocarbonyl group, and $R^3$ is not a halogen atom or hydrogen atom.

11. The multilayer film of claim 9, wherein the SAA-g-PO is a sulfonamide endo-cis-bicyclo[2.2.1]heptane-2,3-dicarboxylic anhydride grafted polyethylene having a Structure (2a):

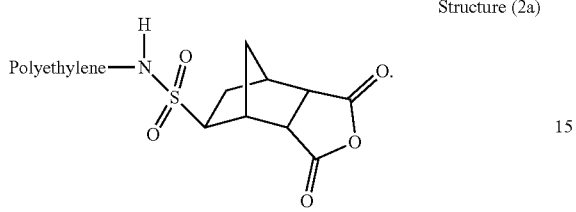

Structure (2a)

12. The multilayer film of claim 9, wherein the SAA-g-PO is a sulfonamide 3-(2,5-dioxotetrahydrofuran-3-yl)-2-methylpropane grafted polyethylene having a Structure (2b):

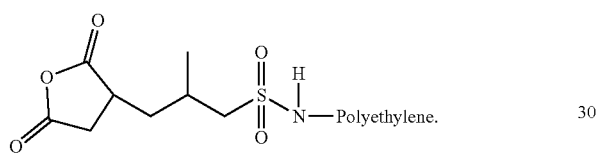

Structure (2b)

13. A multilayer film comprising:
a layer (A) comprising an olefin-based polymer;
a layer (B) that is a tie layer comprising a sulfonamide aliphatic anhydride grafted olefin-based polymer (SAA-g-PO);
a layer (C) comprising a polar component;
a layer (D) that is a tie layer, the layer (D) comprising the SAA-g-PO;
a layer (E) comprising an olefin-based polymer; and
the multilayer film has the structure A/B/C/D/E.

14. The multilayer film of claim 13, wherein the SAA-g-PO has a Structure (2):

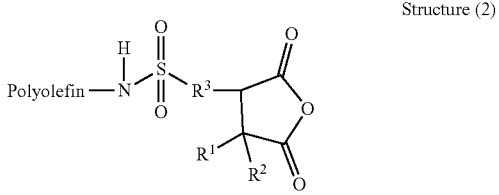

Structure (2)

wherein $R^1$, $R^2$, and $R^3$ may be the same or different; and $R^1$, $R^2$, and $R^3$ each is independently selected from a substituted $C_1$-$C_{40}$ hydrocarbonyl group, an unsubstituted $C_1$-$C_{40}$ hydrocarbonyl group, $Si(R^C)_3$, $OR^C$, $R^CC(O)O$—, $R^COC(O)$—, $R^CC(O)N(R)$—, $(R^C)_2NC(O)$—, a halogen atom, and a hydrogen atom, wherein $R^C$ is a $C_1$-$C_{30}$ hydrocarbonyl group;

with the proviso that at least one of $R^1$, $R^2$, and $R^3$ is selected from a substituted $C_1$-$C_{40}$ hydrocarbonyl group or an unsubstituted $C_1$-$C_{40}$ hydrocarbonyl group, and $R^3$ is not a halogen atom or hydrogen atom.

15. The multilayer film of claim 13, wherein
the layer (A) comprises a polyethylene;
the layer (B) comprises a sulfonamide endo-cis-bicyclo[2.2.1]heptane-2,3-di carb oxylic anhydride grafted polyethylene or a sulfonamide 3-(2,5-dioxotetrahydrofuran-3-yl)-2-methylpropane grafted polyethylene;
the layer (C) comprises a nylon or an ethylene/vinyl alcohol (EVOH) copolymer;
the layer (D) comprises a sulfonamide endo-cis-bicyclo[2.2.1]heptane-2,3-di carb oxylic anhydride grafted polyethylene or a sulfonamide 3-(2,5-dioxotetrahydrofuran-3-yl)-2-methylpropane grafted polyethylene; and
the layer (E) comprises a polyethylene.

* * * * *